US011027038B1

(12) United States Patent
Rhoades et al.

(10) Patent No.: US 11,027,038 B1
(45) Date of Patent: Jun. 8, 2021

(54) FAN FOR IMPROVING AIR QUALITY

(71) Applicant: DELTA T, LLC, Lexington, KY (US)

(72) Inventors: Lennie Rhoades, Nicholasville, KY (US); Eric J. Evans, Lexington, KY (US); Jay Fizer, Lexington, KY (US); Marc McKinzie, Lexington, KY (US); Pete Maley, Lexington, KY (US); Mike Smith, Lexington, KY (US); Jayme Webb, Lexington, KY (US)

(73) Assignee: DELTA T, LLC, Lexington, KY (US)

( * ) Notice: Subject to any disclaimer, the term of this patent is extended or adjusted under 35 U.S.C. 154(b) by 0 days.

(21) Appl. No.: 17/147,086

(22) Filed: Jan. 12, 2021

Related U.S. Application Data

(60) Provisional application No. 63/060,826, filed on Aug. 4, 2020, provisional application No. 63/045,882, filed on Jun. 30, 2020, provisional application No. 63/038,446, filed on Jun. 12, 2020, provisional application No. 63/029,105, filed on May 22, 2020.

(51) Int. Cl.
*A61L 9/22* (2006.01)
*F04D 29/32* (2006.01)
*F04D 13/06* (2006.01)
*F04D 25/08* (2006.01)

(52) U.S. Cl.
CPC ............... *A61L 9/22* (2013.01); *F04D 13/06* (2013.01); *F04D 25/088* (2013.01); *F04D 29/325* (2013.01); *A61L 2209/134* (2013.01)

(58) Field of Classification Search
CPC ...... F04D 13/06; F04D 25/088; F04D 29/325; F04D 29/701; F04D 29/703; A61L 9/22; A61L 2209/134
See application file for complete search history.

(56) References Cited

U.S. PATENT DOCUMENTS

| 2,354,817 A | 8/1944 | Law |
| 4,422,824 A | 12/1983 | Eisenhardt, Jr. |

(Continued)

FOREIGN PATENT DOCUMENTS

| CN | 102225214 B | 10/2011 |
| CN | 202266462 U | 6/2012 |

(Continued)

OTHER PUBLICATIONS

Bolashikov, Z.D. et a;, "Methods for air cleaning and protection of building occupants from airborne pathogens", Building and Environment ,(2009) , vol. 44, pp. 1378-1385.

(Continued)

*Primary Examiner* — Patrick Hamo
(74) *Attorney, Agent, or Firm* — King & Schickli, PLLC

(57) ABSTRACT

A fan is for improving air quality, such as in an indoor environment. The fan includes a motor and a rotatable hub coupled to the motor. At least one fan blade includes a first end portion coupled to the rotatable hub and a second end portion radially distant from the rotatable hub. At least one ion generator is carried by the second end portion of the at least one fan blade, such as by a winglet associated therewith. A stationary tube passes through the rotatable hub including a conduit for transmitting power. A rotary coupling is also provided for transmitting power from the conduit to the at least one ion generator.

30 Claims, 11 Drawing Sheets

(56) References Cited

U.S. PATENT DOCUMENTS

| | | | |
|---|---|---|---|
| 4,559,467 A | 12/1985 | Beckmann et al. | |
| 4,597,781 A * | 7/1986 | Spector | B03C 3/011 96/52 |
| 5,795,131 A * | 8/1998 | Crowhurst | F24F 7/007 416/146 R |
| 5,887,785 A | 3/1999 | Yilmaz | |
| 5,891,399 A | 4/1999 | Owesen | |
| 6,036,331 A * | 3/2000 | Acquisto | F04D 29/005 362/96 |
| 6,176,736 B1 | 1/2001 | Hsu | |
| 6,244,820 B1 | 6/2001 | Yilmaz | |
| 6,247,894 B1 | 6/2001 | Moody et al. | |
| 6,309,083 B1 | 10/2001 | Lathrop et al. | |
| 6,398,970 B1 | 6/2002 | Justel et al. | |
| 6,855,295 B2 | 2/2005 | Kulp | |
| 7,160,566 B2 | 1/2007 | Fink et al. | |
| 7,177,133 B2 | 2/2007 | Riskin | |
| 7,252,478 B2 * | 8/2007 | Aynsley | F03B 17/063 416/204 R |
| 7,407,624 B2 | 8/2008 | Cumberland | |
| 7,449,053 B2 | 11/2008 | Hallam | |
| 7,520,978 B2 | 4/2009 | Harbers | |
| 7,591,962 B2 | 9/2009 | Justel et al. | |
| 7,879,299 B2 | 2/2011 | McEllen | |
| 7,969,707 B2 | 6/2011 | Riskin | |
| 7,988,923 B2 | 8/2011 | Fink et al. | |
| 8,080,203 B2 | 12/2011 | First et al. | |
| 8,097,092 B2 | 1/2012 | Derra et al. | |
| 8,106,367 B2 | 1/2012 | Riskin | |
| 8,114,342 B2 | 2/2012 | Jung et al. | |
| 8,114,346 B2 | 2/2012 | Hyde et al. | |
| 8,124,012 B2 | 2/2012 | Leroux et al. | |
| 8,143,591 B2 | 3/2012 | Gefter et al. | |
| 8,575,838 B2 | 11/2013 | Raas et al. | |
| 8,607,616 B2 | 12/2013 | Marra | |
| 8,611,065 B2 | 12/2013 | Riskin | |
| 8,667,707 B2 | 3/2014 | Date et al. | |
| 8,672,649 B2 | 3/2014 | Smith et al. | |
| 8,747,754 B2 | 6/2014 | Abate | |
| 8,795,590 B1 | 8/2014 | Ellis | |
| 8,834,789 B2 | 9/2014 | Schiene et al. | |
| 8,835,875 B2 | 9/2014 | She et al. | |
| 8,861,167 B2 | 10/2014 | Waddell et al. | |
| 8,877,124 B2 | 11/2014 | Bergman | |
| 8,891,058 B2 | 11/2014 | Metzmacher et al. | |
| D720,446 S | 12/2014 | Ellis | |
| 8,900,519 B2 | 12/2014 | Krosney et al. | |
| 8,921,806 B2 | 12/2014 | Broer et al. | |
| 8,922,971 B2 | 12/2014 | Abate et al. | |
| 8,936,944 B2 | 1/2015 | Peltz et al. | |
| 8,957,571 B2 | 2/2015 | Riskin | |
| 9,045,358 B2 | 6/2015 | Greuel | |
| 9,186,475 B2 | 11/2015 | Arcilla et al. | |
| 9,217,560 B2 | 12/2015 | Harbers et al. | |
| 9,283,295 B2 | 3/2016 | Fink et al. | |
| 9,295,746 B2 | 3/2016 | Ellis | |
| 9,308,289 B2 | 4/2016 | Graff et al. | |
| 9,327,048 B2 | 5/2016 | Deane et al. | |
| 9,365,884 B2 | 6/2016 | Nishikawa et al. | |
| 9,370,599 B2 | 6/2016 | Deane et al. | |
| 9,370,600 B1 | 6/2016 | DuPuis et al. | |
| 9,394,191 B2 | 7/2016 | Darwinkel et al. | |
| 9,399,998 B1 * | 7/2016 | Hardie | F04D 25/088 |
| 9,441,634 B2 | 9/2016 | Spiro | |
| 9,551,497 B2 | 1/2017 | Waddell | |
| 9,579,664 B2 | 2/2017 | Marra | |
| 9,597,424 B2 | 3/2017 | Gurman | |
| 9,839,714 B2 | 12/2017 | Waddell et al. | |
| 9,839,901 B2 | 12/2017 | Ellis et al. | |
| 9,843,169 B2 | 12/2017 | Riskin et al. | |
| 9,847,623 B2 | 12/2017 | Sunshine | |
| 9,849,208 B2 | 12/2017 | Waddell | |
| D811,574 S | 2/2018 | McRoberts | |
| 9,901,039 B1 | 2/2018 | Dellerson et al. | |
| 9,925,567 B2 | 3/2018 | Waddell | |
| 9,931,426 B2 | 4/2018 | Ronda et al. | |
| 9,956,306 B2 | 5/2018 | Brais et al. | |
| 9,976,957 B2 | 5/2018 | Kim et al. | |
| 9,987,499 B2 | 6/2018 | Hayashi et al. | |
| 10,006,619 B1 | 6/2018 | Niemiec et al. | |
| 10,020,180 B2 | 7/2018 | Waddell | |
| 10,071,177 B1 | 9/2018 | Kellogg, Jr. | |
| 10,073,055 B2 | 9/2018 | Waddell | |
| 10,092,771 B2 | 10/2018 | Varghese et al. | |
| 10,101,051 B2 | 10/2018 | Heller | |
| 10,125,971 B2 | 11/2018 | Graziano et al. | |
| 10,128,075 B2 | 11/2018 | Waddell | |
| 10,139,060 B1 | 11/2018 | Erdener et al. | |
| 10,221,080 B2 | 3/2019 | Boamfa et al. | |
| 10,246,817 B2 | 4/2019 | Wang et al. | |
| 10,279,068 B2 | 5/2019 | Eide et al. | |
| 10,363,327 B2 | 7/2019 | Liao et al. | |
| 10,370,695 B2 | 8/2019 | Kanhye | |
| 10,393,399 B2 | 8/2019 | Hilbig et al. | |
| 10,416,377 B2 | 9/2019 | Girotto et al. | |
| 10,439,370 B2 | 10/2019 | Sunshine | |
| 10,443,871 B2 | 10/2019 | Agnaou et al. | |
| 10,453,669 B2 | 10/2019 | Ellis et al. | |
| D868,233 S | 11/2019 | Galbreath et al. | |
| 10,476,276 B2 | 11/2019 | Amelio et al. | |
| 10,501,342 B2 | 12/2019 | Hayashi et al. | |
| 10,508,982 B2 | 12/2019 | Koerber et al. | |
| 10,514,139 B2 | 12/2019 | Athalye | |
| D875,046 S | 2/2020 | Waddell | |
| 10,585,218 B2 | 3/2020 | Ufkes et al. | |
| 10,589,224 B2 | 3/2020 | Verbakel et al. | |
| 10,596,291 B2 | 3/2020 | Van Der Graaf | |
| 10,670,026 B2 | 6/2020 | Niemiec et al. | |
| 10,677,446 B2 | 6/2020 | Spiro | |
| 10,705,005 B2 | 7/2020 | Qi et al. | |
| 10,753,626 B2 | 8/2020 | Skelton | |
| 10,772,980 B2 | 9/2020 | Stibich | |
| 10,808,956 B2 | 10/2020 | Soyyigit | |
| 2003/0230477 A1 | 12/2003 | Fink et al. | |
| 2005/0058584 A1 | 3/2005 | Shyu | |
| 2005/0155366 A1 | 7/2005 | Kim et al. | |
| 2007/0009363 A1 * | 1/2007 | King | F04D 25/088 416/210 R |
| 2007/0111655 A1 | 5/2007 | Song et al. | |
| 2008/0213129 A1 | 9/2008 | van der Pol et al. | |
| 2009/0097975 A1 * | 4/2009 | Aynsley | F04D 29/601 416/32 |
| 2009/0122572 A1 | 5/2009 | Page et al. | |
| 2009/0129974 A1 | 5/2009 | McEllen | |
| 2009/0169438 A1 | 7/2009 | Bruggink | |
| 2009/0294342 A1 | 12/2009 | Bruggink et al. | |
| 2010/0003164 A1 | 1/2010 | Bourne et al. | |
| 2010/0181910 A1 | 7/2010 | Kessels | |
| 2010/0284168 A1 | 11/2010 | Walter et al. | |
| 2011/0103982 A1 * | 5/2011 | A. | F24F 7/007 417/423.9 |
| 2011/0104397 A1 | 5/2011 | Liao et al. | |
| 2011/0286204 A1 | 11/2011 | Lord | |
| 2013/0119266 A1 | 5/2013 | Mondt et al. | |
| 2013/0239803 A1 | 9/2013 | Palmer | |
| 2014/0198426 A1 | 7/2014 | Abate | |
| 2015/0075371 A1 | 3/2015 | Abate | |
| 2015/0110625 A1 | 4/2015 | De Siqueira Indio Da Costa et al. | |
| 2015/0174426 A1 | 6/2015 | St. Germain et al. | |
| 2016/0376170 A1 | 12/2016 | Ivan et al. | |
| 2017/0080373 A1 | 3/2017 | Engelhard | |
| 2017/0232132 A1 | 8/2017 | Deane et al. | |
| 2017/0260681 A1 | 9/2017 | Gao et al. | |
| 2018/0065126 A1 | 3/2018 | Abate et al. | |
| 2018/0072593 A1 | 3/2018 | Verschueren | |
| 2018/0185530 A1 | 7/2018 | Ronda et al. | |
| 2018/0250428 A1 | 9/2018 | Canfield | |
| 2018/0280558 A1 | 10/2018 | Mount | |
| 2019/0047877 A1 | 2/2019 | Geboers et al. | |
| 2019/0091700 A1 | 3/2019 | Hilbig et al. | |
| 2019/0104605 A1 | 4/2019 | Van Abeelen et al. | |
| 2019/0125919 A1 | 5/2019 | Ellis et al. | |
| 2019/0247862 A1 | 8/2019 | Galbreath et al. | |

(56) References Cited

U.S. PATENT DOCUMENTS

| | | |
|---|---|---|
| 2019/0247893 A1 | 8/2019 | Waddell |
| 2019/0264702 A1 | 8/2019 | Huggins et al. |
| 2019/0275189 A1 | 9/2019 | Skelton |
| 2019/0280465 A1 | 9/2019 | Sunshine |
| 2019/0353359 A1 | 11/2019 | Seibold |
| 2020/0009279 A1 | 1/2020 | Janssen |
| 2020/0016288 A1 | 1/2020 | Lalicki et al. |
| 2020/0062622 A1 | 2/2020 | Linley et al. |
| 2020/0166235 A1 | 5/2020 | Marra et al. |
| 2020/0173646 A1 | 6/2020 | Marinus et al. |
| 2020/0179544 A1 | 6/2020 | Ufkes |
| 2020/0188544 A1 | 6/2020 | Ellis et al. |
| 2020/0254125 A1 | 8/2020 | Lloyd |
| 2020/0348038 A1 | 11/2020 | Risbeck et al. |
| 2020/0393159 A1 | 12/2020 | Takayanagi |
| 2020/0408434 A1 | 12/2020 | Arentsen |

FOREIGN PATENT DOCUMENTS

| | | |
|---|---|---|
| CN | 103197659 A | 7/2013 |
| CN | 104154622 A | 11/2014 |
| CN | 104807111 A | 7/2015 |
| CN | 104949317 A | 9/2015 |
| CN | 105107631 A | 12/2015 |
| CN | 205090506 U | 3/2016 |
| CN | 205374368 U | 7/2016 |
| CN | 205446124 U | 8/2016 |
| CN | 106090836 A | 11/2016 |
| CN | 106152279 A | 11/2016 |
| CN | 106438420 A | 2/2017 |
| CN | 106610058 A | 5/2017 |
| CN | 106917765 A | 7/2017 |
| CN | 107181169 A | 9/2017 |
| CN | 107191398 A | 9/2017 |
| CN | 107196192 A | 9/2017 |
| CN | 206582820 U | 10/2017 |
| CN | 107388129 A | 11/2017 |
| CN | 107449073 A | 12/2017 |
| CN | 206947733 U | 1/2018 |
| CN | 107796094 A | 3/2018 |
| CN | 207094939 U | 3/2018 |
| CN | 207098267 U | 3/2018 |
| CN | 207218007 U | 4/2018 |
| CN | 108131616 A | 6/2018 |
| CN | 207962855 U | 10/2018 |
| CN | 208170554 U | 11/2018 |
| CN | 208170584 U | 11/2018 |
| CN | 208174004 U | 11/2018 |
| CN | 108980999 A | 12/2018 |
| CN | 109058136 A | 12/2018 |
| CN | 208205238 U | 12/2018 |
| CN | 109137463 A | 1/2019 |
| CN | 208553675 U | 3/2019 |
| CN | 208674593 U | 3/2019 |
| CN | 109589441 A | 4/2019 |
| CN | 208885567 U | 5/2019 |
| CN | 110379514 A | 10/2019 |
| CN | 209926487 U | 1/2020 |
| CN | 209959513 U | 1/2020 |
| CN | 110748373 A | 2/2020 |
| CN | 111346247 A | 6/2020 |
| CN | 111388715 A | 7/2020 |
| CN | 111554409 A | 8/2020 |
| CN | 111561751 A | 8/2020 |
| CN | 211217848 A | 8/2020 |
| CN | 111637078 A | 9/2020 |
| CN | 111765530 A | 10/2020 |
| CN | 111811067 A | 10/2020 |
| CN | 111912044 A | 11/2020 |
| CN | 112161338 A | 1/2021 |
| DE | 2622749 A1 | 12/1977 |
| EP | 0409337 A1 | 1/1991 |
| EP | 1752715 A1 | 2/2007 |
| EP | 1870114 A1 | 12/2007 |
| EP | 2399614 A1 | 12/2011 |
| EP | 2646740 A2 | 10/2013 |
| EP | 2788680 A2 | 10/2014 |
| EP | 2881126 A1 | 6/2015 |
| EP | 2914858 A1 | 9/2015 |
| EP | 3043431 A1 | 7/2016 |
| EP | 3237857 A1 | 11/2017 |
| EP | 3331652 A1 | 6/2018 |
| EP | 3578886 A1 | 12/2019 |
| ES | 1249340 U | 7/2020 |
| FR | 2880950 A1 | 7/2006 |
| FR | 3048520 A1 | 9/2017 |
| GB | 546005 A | 6/1942 |
| GB | 2515842 A | 1/2015 |
| GB | 2524009 A | 9/2015 |
| GB | 2524116 A | 9/2015 |
| JP | 09314137 | 6/1942 |
| JP | 2005221217 A | 8/2005 |
| JP | 2007232323 A | 9/2007 |
| JP | 2007301117 A | 11/2007 |
| KR | 20010087720 A | 9/2001 |
| KR | 20030021396 A | 3/2003 |
| KR | 20040041266 A | 5/2004 |
| KR | 20070063968 A | 6/2007 |
| KR | 100838319 B1 | 6/2008 |
| KR | 20120079887 A | 7/2012 |
| KR | 20130125004 A | 11/2013 |
| KR | 101526261 B1 | 6/2015 |
| KR | 101578044 B1 | 12/2015 |
| KR | 20160015084 A | 2/2016 |
| KR | 20190021656 A | 3/2019 |
| KR | 101962823 B1 | 7/2019 |
| KR | 20200004967 A | 1/2020 |
| KR | 102103022 B1 | 4/2020 |
| KR | 102192053 B1 | 12/2020 |
| TW | M596286 U | 6/2020 |
| WO | 9913922 A1 | 3/1999 |
| WO | 0212127 A2 | 2/2002 |
| WO | 2005031881 A2 | 4/2005 |
| WO | 2008117224 A1 | 10/2008 |
| WO | 2008139491 A2 | 11/2008 |
| WO | 2009104119 A2 | 8/2009 |
| WO | 2010131398 A1 | 11/2010 |
| WO | 2011013083 A1 | 2/2011 |
| WO | 2012069963 A1 | 5/2012 |
| WO | 2012071598 A2 | 6/2012 |
| WO | 2012120391 A1 | 9/2012 |
| WO | 2013036414 A1 | 3/2013 |
| WO | 2015110367 A1 | 7/2015 |
| WO | 2015132367 A1 | 9/2015 |
| WO | 2015132368 A1 | 9/2015 |
| WO | 2016077403 A1 | 5/2016 |
| WO | 2016200047 A1 | 12/2016 |
| WO | 2017021504 A1 | 2/2017 |
| WO | 2017055093 A1 | 4/2017 |
| WO | 2017144323 A1 | 8/2017 |
| WO | 2017152694 A1 | 9/2017 |
| WO | 2017162453 A1 | 9/2017 |
| WO | 2017211773 A1 | 12/2017 |
| WO | 2017216056 A1 | 12/2017 |
| WO | 2018060047 A1 | 4/2018 |
| WO | 2018065467 A1 | 4/2018 |
| WO | 2019045212 A1 | 3/2019 |
| WO | 2019081651 A1 | 5/2019 |
| WO | 2019091987 A1 | 5/2019 |
| WO | 2020050864 A1 | 3/2020 |
| WO | 2020113149 A1 | 6/2020 |

OTHER PUBLICATIONS

Heidarinejad, Mohammad et al, "Computational fluid dynamics modelling of UR-UVGI lamp effectiveness to promote disinfection of airborne microorganisms", World Review of Science, Technology and Sust. Development, 2013, vol. 10, Nos. 112/3, pp. 78-95.

Li, Chan et al, "Simulations to Determine the Disinfection Efficiency of Supplementary UV Light Devices in a Ventilated Hospital Isolation Room", Indoor and Built Environment, 2010, vol. 19,1, pp. 48-56.

(56) References Cited

OTHER PUBLICATIONS

Li, Yanju et al, A Study on the Decontaminated Efficiency of Ultraviolet Device on the Indoor Airborne Bacteria, Science Direct—Procedia Engineering, 2017, vol. 205, pp. 1376-1380, www.sciencedirect.com.
Momoi, Y. et al, "Modeling of Ceiling Fan Based on Velocity Measurement for CFD Simulation of Airflow in Large Room", 1Osaka University, Graduate School of Eng., Dept of Architectural Eng., 2004, pp. 1-6.
Momoi, Y. et al, "Modeling of Prescribed Velocity Generated by Ceiling Fan Based on Velocity Measurement for CFD Simulation", 2007, pp. 1-10, : https:/jwww.researchgate.netjpublicationj238069434.
Noakes, C.J. et al. "Development of a numerical model to simulate the biological inactivation of airborne microorganisms in the presence of ultraviolet light", Journal of Aerosol Science, 2004, vol. 35, pp. 489-507.
Noakes, C.J. et al, "Modelling the Performance of Upper Room Ultraviolet Germicidal Irradiation Devices in Ventilated Rooms: Comparison of Analytical and CFD Methods", Indoor and Built Environment, 2004, vol. 13, pp. 477-488.
Noakes, C.J. et al, "Use of CFD Modelling to Optimise the Design of Upper-room UVGI Disinfection Systems for Ventilated Rooms", Indoor and Built Environment, 2006, vol. 15, pp. 347-356.
Pichurova, George et al, "A validated numerical investigation of the ceiling fan's role in the upper-room UVGI efficacy", Building and Environment, 2015, vol. 86, pp. 109-119.
Sung, M et al, "Method to evaluate UV dose of upper-room UVGI system using the concept of ventilation efficiency", Building and Environment, 2010, vol. 45, pp. 1626-1631.
Wang, Bei et al, "Evaluation of Modeling and Measurement Techniques of Ultraviolet Germicidal Irradiation Effectiveness—Towards the Design of Immune Buildings", Indoor and Built Environment, 2009, vol. 18:2, pp. 101-112.
Wu, C.L. et al, "A new mathematical model for irradiance field prediction of upper-room ultraviolet germicidal systems", Journal of Hazardous Materials, 2011, vol. 189, pp. 173-185.
Yang, Yi et al, "Numerical Modelling to Evaluate the Disinfection Efficacy of Multiple Upper-Room Ultaviolet Germicidal Fixtures System", Science Direct—Procedia Engineering, 2015, vol. 121, pp. 1657-1664.
Zhu, Shengwei et al, "Numerical modeling of indoor environment with a ceiling fan and an upper-room ultraviolet germicidal irradiation system", Building and Environment, 2014, vol. 72, pp. 116-124.
Rudnick, Stephen N. et al, "A Simple Method for Evaluating the Performance of Louvered Fixtures Designed for Upper-Room Ultraviolet Germicidal Irradiation", The journal of the Illuminating Engineering Society of North America, 2017, vol. 13:2, pp. 91-105.
Rudnick, S. N. et al,"Influence of ceiling fan's speed and direction on efficacy of upperroom, ultraviolet germicidal irradiation: Experimental", Building and Environment, 2015, vol. 92, pp. 756-763.
Zhu, Shengwei et al, "Numerical Investigation of Upper-Room UVGI Disinfection Efficacy in an Environmental Chamber with a Ceiling Fan", Photochemistry and Photobiology, 2013, 89: 782-791.
English Translation for DE2622749A1 dated Dec. 8, 1977.
English Translation for KR20010087720A dated Sep. 21, 2001.
English Translation for KR20030021396A dated Mar. 15, 2003.
English Translation for KR20040041266A dated May 17, 2004.
English Translation for KR20070063968A dated Jun. 20, 2007.
English Abstract for EP2881126A1 dated Jun. 10, 2015.
English Translation for ES1249340U dated Jul. 13, 2020.
English Translation for FR2880950A1 dated Jul. 21, 2006.
English Translation for FR3048520 dated Sep. 8, 2017.
English Translation for JP2005221217A dated Aug. 18, 2005.
English Translation for JP2007301117A dated Nov. 22, 2007.
English Translation for KR100838319B1 dated Jun. 13, 2008.
English Translation for KR101962823B1 dated Jul. 31, 2019.
English Translation for KR102103022B1 dated Apr. 21, 2020.
English Translation for KR102192053B1 dated Dec. 16, 2020.
English Translation for KR20120079887A dated Jul. 16, 2012.
English Translation for KR20130125004A dated Nov. 18, 2013.
English Translation for KR20200004967A dated Jan. 15, 2020.
English Abstract for WO2017021504A1 dated Feb. 9, 2017.
English Translation for WO2017152694A1 dated Sep. 14, 2017.
English Translation for WO2019045212A1 dated Mar. 7, 2019.
English Abstract for CN105107631A dated Dec. 2, 2015.
English Abstract for CN107181169A dated Sep. 19, 2017.
English Abstract for CN107196192A dated Sep. 22, 2017.
English Abstract for CN109137463A dated Jan. 4, 2019.
English Abstract for CN109589441A dated Apr. 9, 2019.
English Abstract for CN205090506U dated Mar. 16, 2016.
English Abstract for CN206947733U dated Jan. 30, 2018.
English Abstract for CN207094939U dated Mar. 13, 2018.
English Translation for CN207098267U dated Mar. 13, 2018.
English Translation for CN207218007U dated Apr. 10, 2018.
English Translation for CN208170554U dated Nov. 30, 2018.
English Translation for CN208174004U dated Nov. 30, 2018.
English Translation for CN208205238U dated Dec. 7, 2018.
English Translation for CN208553675U dated Mar. 1, 2019.
English Translation for CN208674593U dated Mar. 29, 2019.
English Translation for CN103197659A dated Jul. 10, 2013.
English Translation for CN104154622A dated Nov. 19, 2014.
English Translation for CN104807111A dated Jul. 29, 2015.
English Translation for CN104949317A dated Sep. 30, 2015.
English Translation for CN106090836A dated Nov. 9, 2016.
English Translation for CN106152279A dated Nov. 13, 2016.
English Translation for CN107191398A dated Sep. 22, 2017.
English Translation for CN107449073A dated Dec. 8, 2017.
English Translation for CN107796094A dated Mar. 13, 2018.
English Translation for CN108131616A dated Jun. 8, 2018.
English Translation for CN108980999A dated Dec. 11, 2018.
English Translation for CN109058136A dated Dec. 21, 2018.
English Translation for CN110379514A dated Oct. 25, 2019.
English Translation for CN110748373A dated Apr. 20, 2020.
English Translation for CN111346247A dated Jun. 30, 2020.
English Translation for CN111388715A dated Jul. 10, 2020.
English Translation for CN111554409A dated Aug. 18, 2020.
English Translation for CN111561751A dated Aug. 21, 2020.
English Translation for CN111637078A dated Sep. 8, 2020.
English Translation for CN111765530A dated Oct. 13, 2020.
English Translation for CN111811067A dated Oct. 23, 2020.
English Translation for CN111912044A dated Nov. 10, 2020.
English Translation for CN112161338A dated Jan. 1, 2021.
English Translation for CN205374368U dated Jul. 6, 2016.
English Translation for CN206582820U dated Oct. 24, 2017.
English Translation for CN207962855U dated Oct. 12, 2018.
English Translation for CN208170584U dated Nov. 30, 2018.
English Translation for CN209926487U dated Jan. 10, 2020.
English Translation for CN211217848A dated Aug. 11, 2020.

\* cited by examiner

FAN FOR IMPROVING AIR QUALITY

This patent application claims the benefit of U.S. Provisional Patent Application Nos. 63/060,826, 63/045,882, 63/038,446, and 63/029,105, the disclosures of which are incorporated herein by reference.

TECHNICAL FIELD

This application relates to the air circulation arts and, more particularly, to a fan adapted for improving air quality, such as by minimizing the presence of airborne germs or pathogens.

BACKGROUND

A variety of fan systems have been made and used over the years in a variety of contexts. For instance, various ceiling fans are disclosed in U.S. Pat. No. 7,284,960, entitled "Fan Blades," issued Oct. 23, 2007; U.S. Pat. No. 6,244,821, entitled "Low Speed Cooling Fan," issued Jun. 12, 2001; U.S. Pat. No. 6,939,108, entitled "Cooling Fan with Reinforced Blade," issued Sep. 6, 2005; and U.S. Pat. No. D607,988, entitled "Ceiling Fan," issued Jan. 12, 2010. The disclosures of each of those U.S. patents are incorporated by reference herein. Additional exemplary fans are disclosed in U.S. Pat. Pub. No. 2008/0008596, entitled "Fan Blades," published Jan. 10, 2008; U.S. Pat. Pub. No. 2009/0208333, entitled "Ceiling Fan System with Brushless Motor," published Aug. 20, 2009; and U.S. Pat. Pub. No. 2010/0278637, entitled "Ceiling Fan with Variable Blade Pitch and Variable Speed Control," published Nov. 4, 2010, the disclosures of which are also incorporated by reference herein. It should be understood that teachings herein may be incorporated into any of the fans described in any of the above-referenced patents, publications, or patent applications. It should also be understood that a fan may include sensors or other features that are used to control, at least in part, operation of a fan system. For instance, such fan systems are disclosed in U.S. Pat. Pub. No. 2009/0097975, entitled "Ceiling Fan with Concentric Stationary Tube and Power-Down Features," published Apr. 16, 2009, the disclosure of which is incorporated by reference herein; U.S. Pat. Pub. No. 2009/0162197, entitled "Automatic Control System and Method to Minimize Oscillation in Ceiling Fans," published Jun. 25, 2009, the disclosure of which is incorporated by reference herein; and U.S. Pat. Pub. No. 2010/0291858, entitled "Automatic Control System for Ceiling Fan Based on Temperature Differentials," published Nov. 18, 2010, the disclosure of which is incorporated by reference herein. Alternatively, any other suitable control systems/features may be used in conjunction with embodiments described herein.

In some environments, it is desirable to eliminate airborne diseases and disease vectors from the air. Existing methods for reducing airborne disease transmission between room occupants include fresh air ventilation, filtration, and direct deactivation/destruction methods such as irradiation or oxidation of the pathogens themselves. For instance, this can be achieved through the use of an air ionizer or ion generator, which is a device that uses high voltage energy to ionize (electrically charge) air molecules. Airborne particles become charged as they attract charged ions from the ionizer by electrostatic attraction. The particles in turn are then attracted to any nearby earthed (grounded) conductors, such as plates within an air cleaner, or simply the nearest walls and ceilings, and disabled as a result.

As can be appreciated, any germicidal fixture positioned in a space is somewhat effective, but obviously limited in efficacy per se given its stationary nature (and the use of multiple stationary devices may be considered costly and inefficient in most applications). In many applications, such stationary devices do not receive enough airflow as a result of circulation because a typical fan is designed for force air toward the floor, and not necessarily to any generators of germicidal energy (which would typically be mounted on the ceiling or walls). Furthermore, many of past approaches are not implemented successfully due to lack of operator training, maintenance issues, sub-par user interfaces and experiences, and cost.

Accordingly, a need is identified for an improved manner of providing a fan with a germicidal capability. In particular, the fan would for part of a system providing a degree of automation of operating certain sterilizing functions that avoids the problems associated with the above-mentioned approaches. Additional aspects of germicidal fans are also disclosed.

SUMMARY

According to a first aspect of the disclosure, a fan for improving air quality is provided. The fan includes a motor, a rotatable hub coupled to the motor, and at least one fan blade comprising a first end coupled to the rotatable hub, a second end radially distant from the rotatable hub, and a winglet attached to the second end. At least one ion generator is carried by the winglet.

In one embodiment, the at least one ion generator is mounted to an inner face of the winglet. The at least one ion generator may be mounted to the winglet below a plane of the at least one fan blade. A rotary coupling may be provided for transmitting power to the at least one ion generator.

A stationary tube passing through the hub may be provided for conveying power to the at least one ion generator, the rotary coupling being connected to the stationary tube. A conduit for supplying power for the ion generator passes from the hub, along the at least one fan blade, and to the winglet to connect to the at least one ion generator. The at least one blade may include a passage extending from the first end to the second end, the passage including wires for transmitting power to the at least one ion generator through the winglet.

The fan may include a plurality of fan blades coupled to the rotatable hub, each having a winglet including an ion generator. The at least one fan blade has a length of greater than about six feet.

According to a further aspect of the disclosure, a fan is provided for improving air quality. The fan includes a motor, a rotatable hub coupled to the motor, and at least one fan blade comprising a first end coupled to the rotatable hub and a second end radially distant from the rotatable hub. The fan further includes at least one ion generator carried by the fan blade at a second end thereof.

In one embodiment, the fan further includes a winglet at the second end of the fan blade for carrying the at least one ion generator. The ion generator may be mounted to an inner face of the winglet, or below a plane of the at least one fan blade. A rotary coupling is provided for transmitting power to the at least one ion generator. A stationary tube passes through the hub for conveying power to the at least one ion generator, the rotary coupling being connected to the stationary tube. A conduit is provided for supplying power for the ion generator, which conduit passes from the hub, along the at least one fan blade, and to the at least one ion generator. The at least one blade includes a passage extending from the first end to the second end, the passage including wires for transmitting power to the at least one ion generator through the winglet.

According to a further aspect of the disclosure, a fan for improving air quality is provided. The fan comprises a motor, a rotatable hub coupled to the motor, and at least one fan blade including a first end coupled to the rotatable hub and a second end radially distant from the rotatable hub. At least one generator for generating germicidal energy is also provided. A stationary tube passes through the rotatable hub including a conduit for transmitting power, and a rotary coupling is provided for transmitting power from the conduit to the at least one ion generator.

Still a further aspect of the disclosure relates to a fan for improving air quality. The fan includes a motor, a rotatable hub coupled to the motor, and at least one fan blade comprising: i, a first end portion coupled to the rotatable hub, ii, a second end portion radially distant from the rotatable hub. At least one ion generator is carried by and located external of the fan blade, such as at the second end portion of the fan blade.

BRIEF DESCRIPTION OF THE DRAWING FIGURES

While the specification concludes with claims which particularly point out and distinctly claim the invention, it is believed the aspects of the disclosure will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
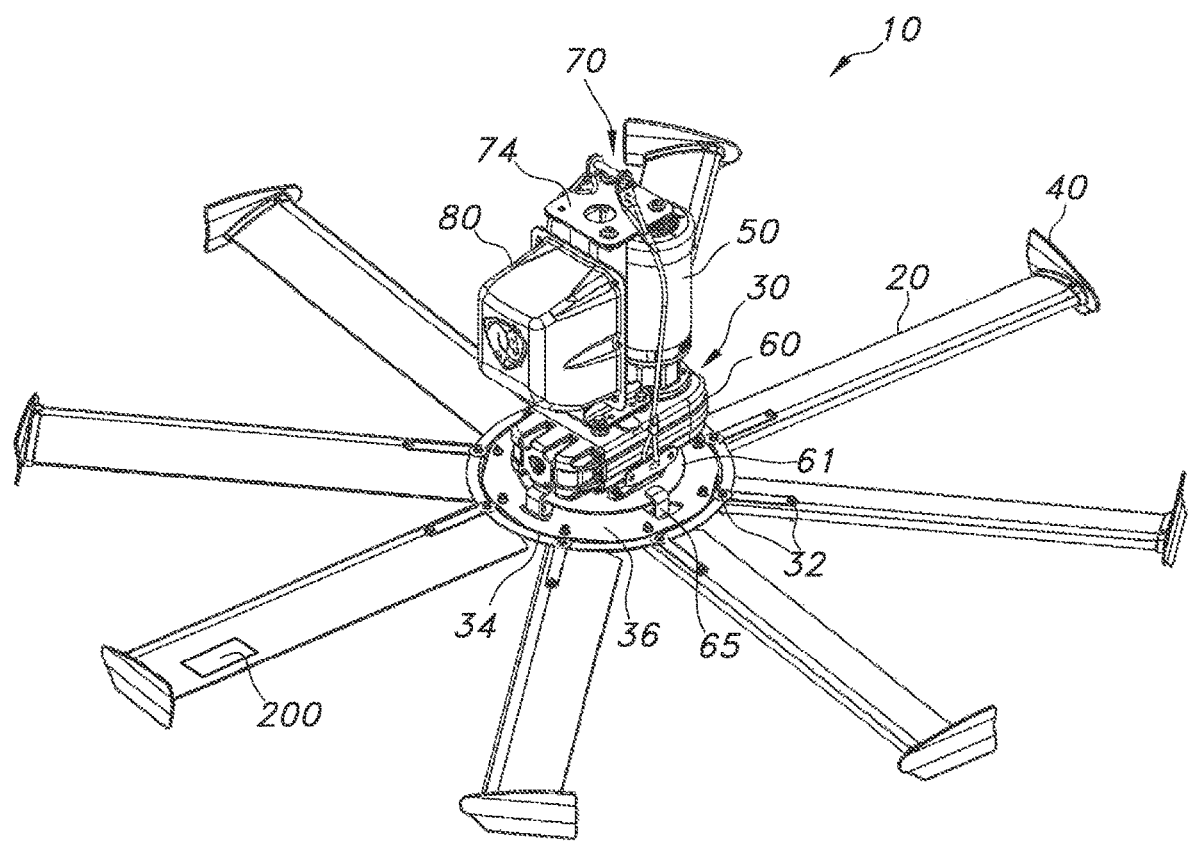
FIG. 1 depicts a perspective view an exemplary fan.

FIG. 1 shows a merely exemplary fan 10. Fan 10 of this example comprises fan blades 20 and a rotating hub 30. Winglets 40 are secured to the outer end 22 of each fan blade 20, and thus form a portion thereof, and establish an end surface or cap to the fan blade 20, which are noted below is typically hollow and formed of a continuous piece of material. In this example, fan 10 also includes a motor 50 and a gearbox 60 that rotationally drive hub 30, a mounting member 70 by which fan 10 may be mounted to a ceiling or other structure; and a control box 80.

Fan blades 20 of the present example are substantially hollow and are formed of extruded aluminum having an airfoil shaped cross-section with a solid body, including a solid leading edge and solid trailing edge, which may be formed of extruded aluminum, though any other suitable configurations, manufacturing techniques, and/or material (s) may be used. By way of example only, fan blades 20 may be configured in accordance with any of the teachings in U.S. Pat. No. 7,284,960, entitled "Fan Blades," issued Oct. 23, 2007, the disclosure of which is incorporated by reference herein. Alternatively, fan blades (20) may be configured in accordance with any of the teachings in U.S. Pub. No. 2008/0008596, entitled "Fan Blades," published Jan. 10, 2008, the disclosure of which is incorporated by reference herein. In other versions, fan blades 20 are configured in accordance with any of the teachings in U.S. Pat. No. 6,244,821, entitled "Low Speed Cooling Fan," issued Jun. 12, 2001, the disclosure of which is incorporated by reference herein. In still other versions, fan blades (20) are configured in accordance with any of the teachings in U.S. Pat. No. 6,939,108, entitled "Cooling Fan with Reinforced Blade," issued Sep. 6, 2005, the disclosure of which is incorporated by reference herein.

Fan blades 20 may define a diameter of fan 10 of approximately 6 feet, approximately 8 feet, approximately 12 feet, or approximately 24 feet. Alternatively, fan 10 may have any other suitable diameter defined by fan blades 20. Furthermore, other suitable configurations for fan blades 20 will be apparent to those of ordinary skill in the art in view of the teachings herein.

Hub 30 of the present example comprises a plurality of mounting members (see element 30a in FIG. 2), which radiate outwardly from hub 30. Each mounting member is inserted into a respective fan blade 20, and the two are secured together with a pair of fasteners 32. Suitable configurations for a hub and methods for attaching a fan blade to a hub are disclosed in U.S. Pat. No. 7,284,960, entitled "Fan Blades," issued Oct. 23, 2007, the disclosure of which is incorporated by reference herein. Of course, any other suitable components, features, devices, or techniques may be used to secure fan blades 20 to hub 30.

Hub 30 is secured to a hub mounting flange 36 by a plurality of fasteners (not shown), though any other suitable components, features, devices, or techniques may be used to secure hub 30 to hub mounting flange 36. Hub 30 thus rotates unitarily with hub mounting flange 36. Hub mounting flange 36 is secured to output shaft 100 by a plurality of fasteners 38. Hub mounting flange 36 (and, therefore, hub 30) thus rotates unitarily with output shaft 100. Again, though, any other suitable components, features, devices, or techniques may be used to secure hub mounting flange 36 to output shaft 100. Furthermore, in some versions, hub mounting flange 36 is omitted, such that hub 30 is secured directly to output shaft 10. Other suitable components and configurations for providing rotation of hub 30 by an output shaft 100 will be apparent to those of ordinary skill in the art in view of the teachings herein.

Several retainers 34 are also secured to fan blades 20 in the present example. By way of example only, such retainers 34 may reduce the likelihood of a fan blade 20 flying off of hub 30 in the event that a hub mounting member breaks free from hub 30 or otherwise fails. However, as with other components described herein, retainers 34 are merely optional, and may be varied, substituted, supplemented, or omitted as desired.

Figure 3:
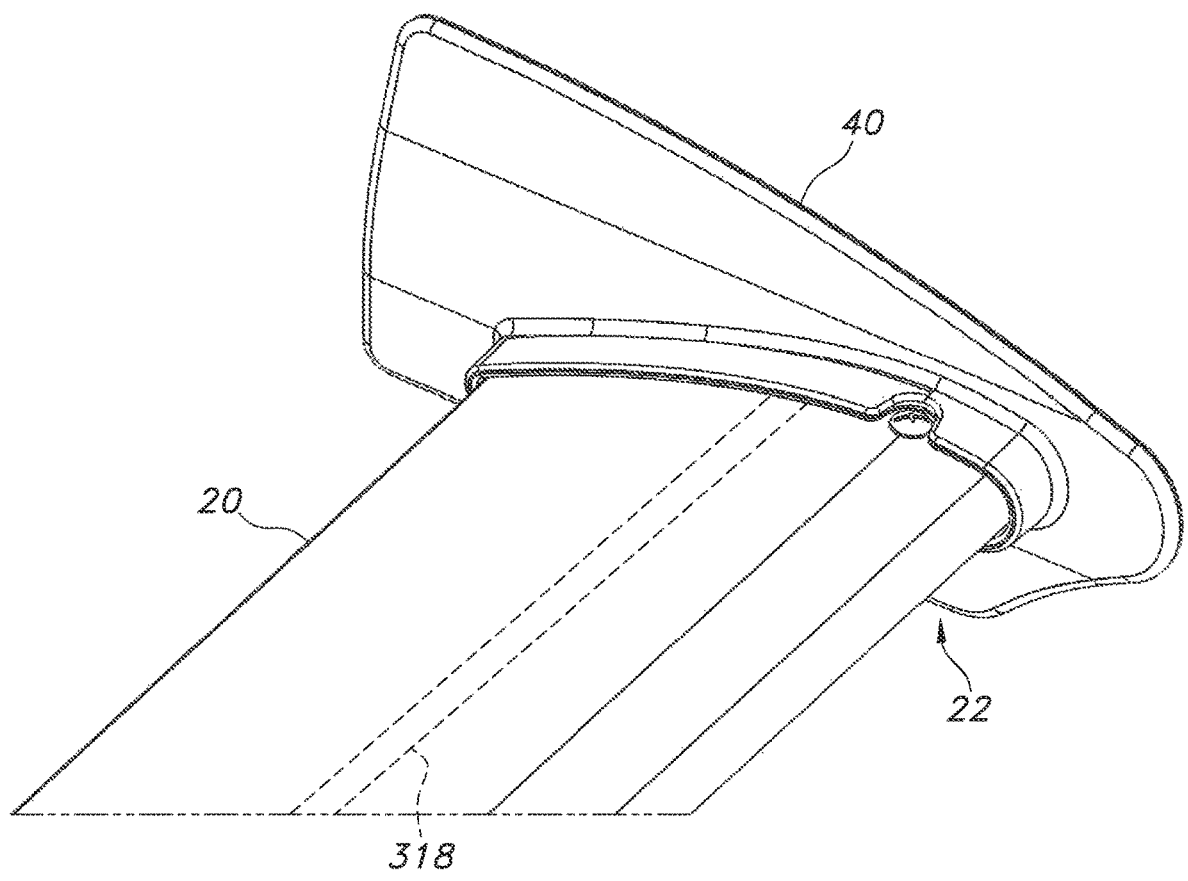
FIG. 3 is a partially cutaway view of a fan blade including a winglet.
Figure 4:
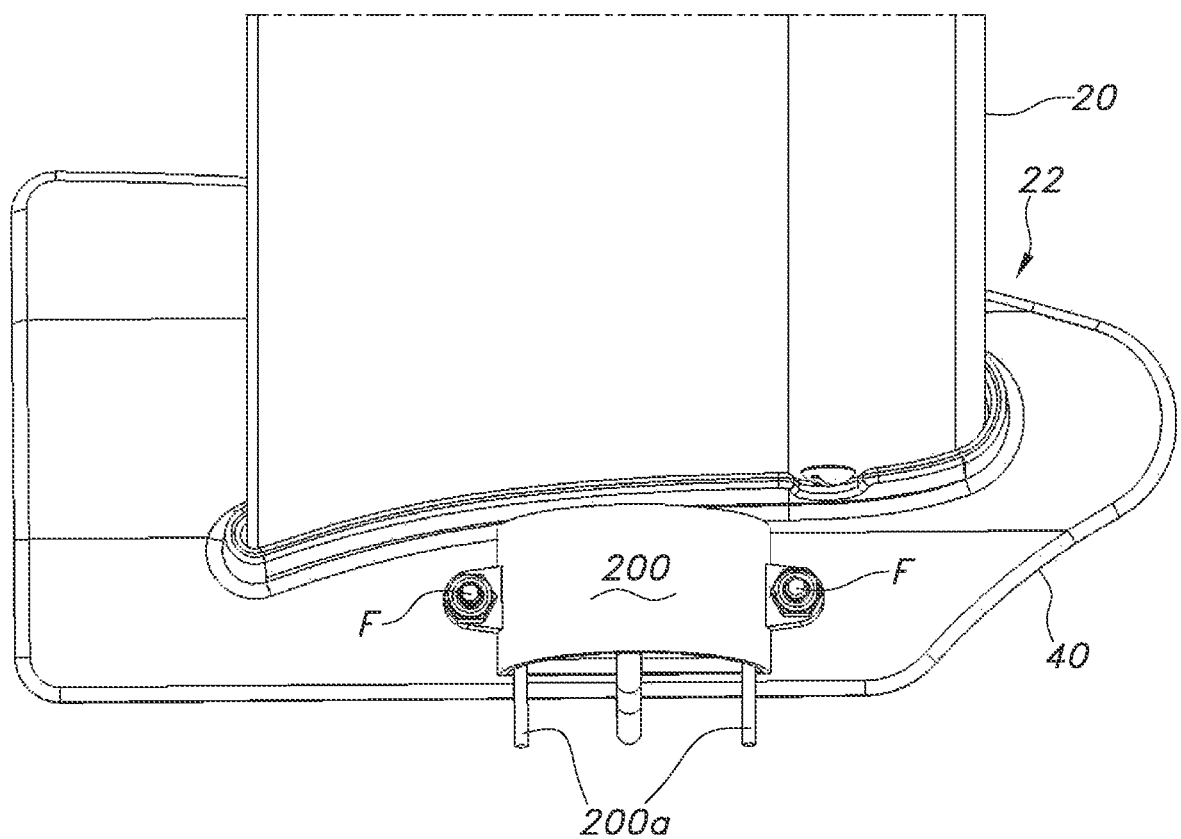
FIGS. 4 and 4A are partially cutaway views of a germicidal generator mounted to the winglet.

Winglets 40 may be configured in accordance with any of the teachings in U.S. Pat. No. 7,252,478, entitled "Fan Blade Modifications," issued Aug. 7, 2007, the disclosure of which is incorporated by reference herein. Alternatively, winglets 40 may be configured to include a cuff 40a, as shown in FIGS. 3-4, in accordance with any of the teachings in U.S. Pub. No. 200810014090, entitled "Cuffed Fan Blade Modifications." published Jan. 17, 2008, the disclosure of which is incorporated by reference herein. In other versions, winglets 40 are configured in accordance with any of the teachings in U.S. Pub. No. 2008/0213097, entitled "Angled Airfoil Extension for Fan Blade," published Sep. 4, 2008, the disclosure of which is incorporated by reference herein. Still other suitable configurations for winglets 40 will be apparent to those of ordinary skill in the art in view of the teachings herein.

Motor 50 may have an external stator (not shown) with windings; and a rotor without windings. The rotor may be coupled with the output shaft 100, which rotates unitarily with the rotor. Motor 50 of the present example may be configured to provide a maximum output power to gearbox 60 of approximately one to approximately two or approximately three horsepower (all inclusive): and a maximum output speed between approximately 1,750 RPM, inclusive, and approximately 3,500 RPM, inclusive. Alternatively, motor 50 may provide any other desired output power and/or output speed.

Motor 50 also includes a control interface, through which motor 50 receives commands from control box 80, as will be described in greater detail below. Motor 50 may also send data to control box 80 via control interface in some versions, including but not limited to data indicative of motor temperature, speed, etc., though such communications are not necessary in all versions. Communication through control interface may thus be unidirectional or bi-directional. It should be understood that motor 50 may be varied in any number of ways. By way of example only, motor 50 may have an internal stator and an external rotor, and may omit gearbox. Still other ways in which motor 50 may be varied will be apparent to those of ordinary skill in the art in view of the teachings herein.

If present, gearbox 60 of the present example may be a mechanical gearbox, and is configured to transfer rotary motion from motor 50 to the hollow output shaft 100 secured to hub mounting flange 36. In particular, gearbox 60 includes gears (not shown) that are in a parallel arrangement and are configured to provide a gear ratio of approximately 38:1 in the present example. Alternatively, any other suitable ratio may be used. In the present example, output shaft 10 is driven by a gear (not shown) that is coaxial with output shaft 100 and shrink/press fit to output shaft 100. Suitable structures and configurations for such gears and shafts will be apparent to those of ordinary skill in the art in view of the teachings herein, as will other suitable contents of and arrangements within a gearbox 60 (to the extent that a gearbox 60 is used at all).

In some versions, motor 50 and gearbox 60 are configured such that the maximum rotational speed of fan 10 is between approximately 125 RPM, inclusive, and approximately 250 RPM, inclusive. For instance, a maximum rotational speed of approximately 180 RPM may be used. In some other versions, a maximum rotational speed may be between approximately 50 RPM, inclusive, and approximately 100 RPM, inclusive. For instance, a maximum rotational speed of approximately 82 RPM may be used. In other versions, a maximum rotational speed may be between approximately 35 RPM, inclusive, and approximately 55 RPM. For instance, a maximum rotational speed of approximately 42 RPM may be used. Of course, any other suitable rotational speed may be used.

Figure 2:
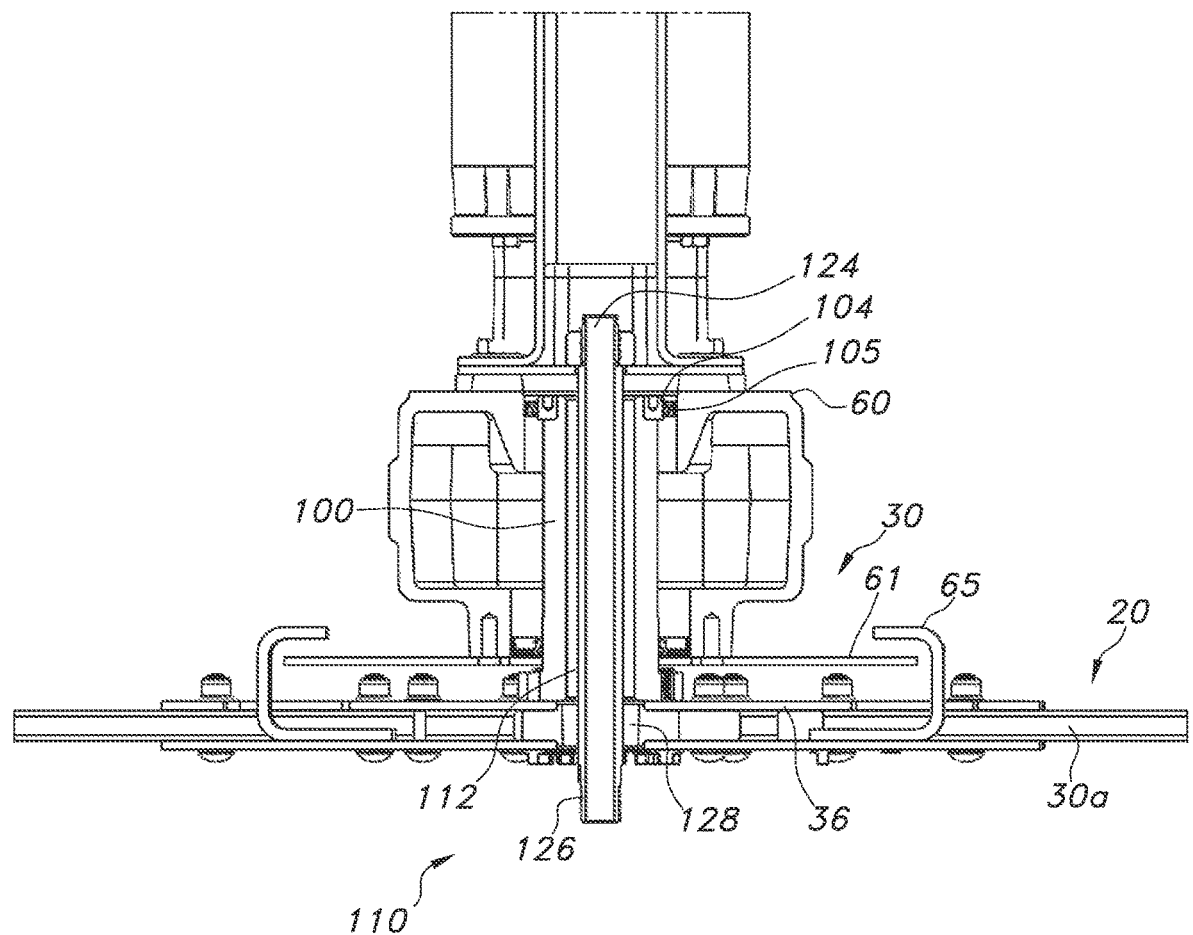
FIG. 2 depicts a partial perspective cross-sectional view of the drive assembly of the fan system of FIG. 1.

As shown in FIGS. 1-2, a plate 61 is secured to the bottom of the housing of gearbox 60. By way of example only, plate 61 may be formed of steel or any other suitable material or combination of materials. As shown in FIG. 1, several brackets 65 extend inwardly from hub 30. Brackets 65 are configured such that they extend over the top of plate 61 without contacting plate 61 during normal operation of fan 10. Brackets 65 may thus rotate with hub 30 without contacting the top of plate 61, such that the radially inwardmost portions of brackets 65 instead essentially "hover" over plate 61, as perhaps best understood from FIG. 2. Brackets 65 are further configured such that, in the event that hub 30 decouples from hub mounting flange 36, or in the event that hub mounting flange 36 decouples from output shaft 100, brackets will catch on plate 61 to prevent such components from falling completely free of the upper portions of fan 10. Plate 61 and brackets 65 may thus provide a safety measure in case of failure of fasteners or other components of fan 10. As with other components described herein, however, plate 61 and brackets 65 are merely optional, and may have any other suitable components, features, or configurations as desired.

Mounting member 70 of the present example comprises a flange 74 is configured to be secured to a ceiling or other structure. In the present example, mounting member 70 is formed of metal, though any other suitable material or combinations may be used. Mounting member 70 may have any other suitable features, components, or configurations. By way of example only, mounting member 70 may be configured in accordance with the teachings of U.S. Non-Provisional patent application Ser. No. 12/203,960, entitled "Ceiling Fan with Angled Mounting." filed Sep. 4, 2008, the disclosure of which is incorporated by reference herein. For instance, the device described in that patent application may be secured to upper flange 74; or directly to gearbox 60 in lieu of having mounting member 70 as shown. Still other suitable structures, devices, and techniques for mounting fan 10 to a ceiling or other structure will be apparent to those of ordinary skill in the art in view of the teachings herein.

As noted above, and as shown in FIG. 2, gearbox 60 provides a drive output through hollow output shaft 100. Hollow output shaft 100 is coupled with hub mounting flange 36 by a plurality of fasteners, such that hub mounting flange 36 (and, consequently, hub 30) rotates unitarily with output shaft 100. Alternatively, any other suitable devices, features, or techniques may be used to secure output shaft 100 to hub mounting flange 36, including but not limited to welding. An upper bearing 104 and an upper seal 105 may be provided between output shaft 100 and the housing of gearbox 60, such that output shaft 100 may rotate freely relative to the housing of gearbox 60 without any lubricant loss from gearbox 60.

A stationary tube 110 is positioned coaxially within output shaft 100. While stationary tube 110 is shown as having a generally circular cross section, stationary tube 110 may have any other suitable shape. A gap 112 is provided between the outer wall of stationary tube 110 and the inner wall of output shaft 100, such that output shaft 100 may rotate freely about stationary tube 110 without causing rotation of stationary tube 110.

Stationary tube 110 defines a central opening 124, through which wires, cables, plumbing, etc. may be passed. As shown in FIG. 2, stationary tube 110 is substantially longer than output shaft 100. In particular, a lower end 126 of stationary tube 110 protrudes downwardly past hub mounting flange 36 and the lower plane defined by hub 30, and through a lower bearing 128. Lower end 126 of stationary tube 110 is threaded in this example, though such threading is not necessary. Exposed lower end 126 may be used to mount a variety of components. It should be understood that since stationary tube 110 does not rotate, and is instead rotationally fixed relative to rotating components of fan 10, anything mounted to lower end 126 will also not rotate in this example.

It should be understood from the foregoing that stationary tube 110 may provide both a non-rotating feature (e.g., lower end 126, etc.) for attaching a variety of accessories to a fan system (10) and a passage (e.g., opening 124, etc.) through which electricity, further structural support. fluids, etc. may be provided to such accessories. Furthermore, output shaft 100, gearbox 60, hub 30, and associated components may provide rotation to drive fan blades 20 without substantially interfering with the above-noted aspects of stationary tube 110.

According to one aspect of the present disclosure, and turning to FIGS. 3-7, the fan 10 may be provided with one or more dynamic germicidal generators, such as in the form of ion generators 200 mounted to a movable portion of the fan 10. such as anywhere along one or more of the blades 20 (see FIG. 1). The dynamic mounting of the ion generator(s) 2 is advantageous in that such increases the number of ions generated (such as by the associated brushes 200a depending therefrom) and hence the efficacy of germicidal action. Indeed, in some one embodiment, the generator(s) 200 may be located adjacent to or at the radially outward end of the associated blade 20 (see, e.g., FIG. 1), where the airspeed is at a maximum or at least a higher value as compared to at the center of the fan 10. An exemplary ion generator 200 suitable for use is manufactured by Plasma Air International (Model: PA601, 12V DC) of Stamford. Conn., which device includes projecting brushes 200a that generate both positive and negative ions. This particular generator consumes little power, is lightweight and presents a low-profile so as to create a negligible impact on the operation of fan 10 in terms of generating air movement in an efficient manner.

Figure 4A:
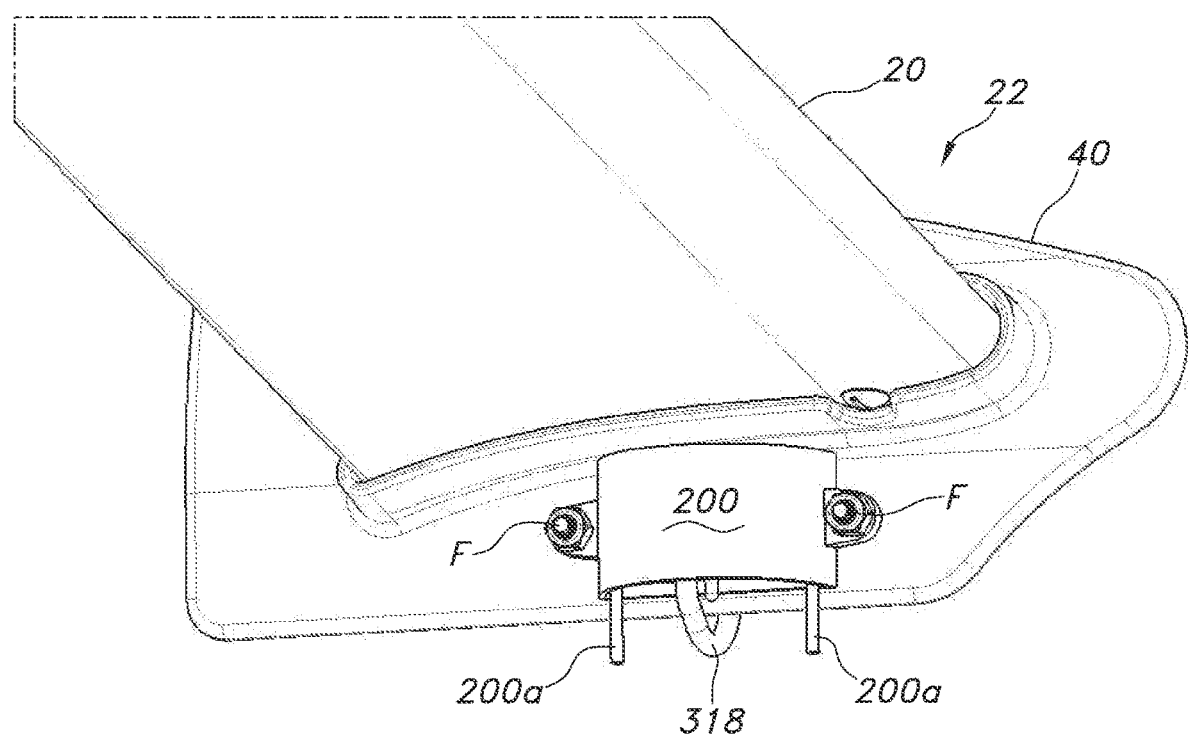

In one exemplary embodiment, the winglet 40 associated with the outer end 22 of each fan blade 20 carries the generator 20. The generator 2 may be connected anywhere along the winglet 40, such as for example on a depending portion and underneath the plane of the blade 20, as shown in FIGS. 4-4A. The connection of the generator 200 to the individual winglet 40 may be achieved using fasteners F. which may pass through the body of the winglet 40, as understood from viewing FIGS. 4, 4A, and 5.

Figure 6:
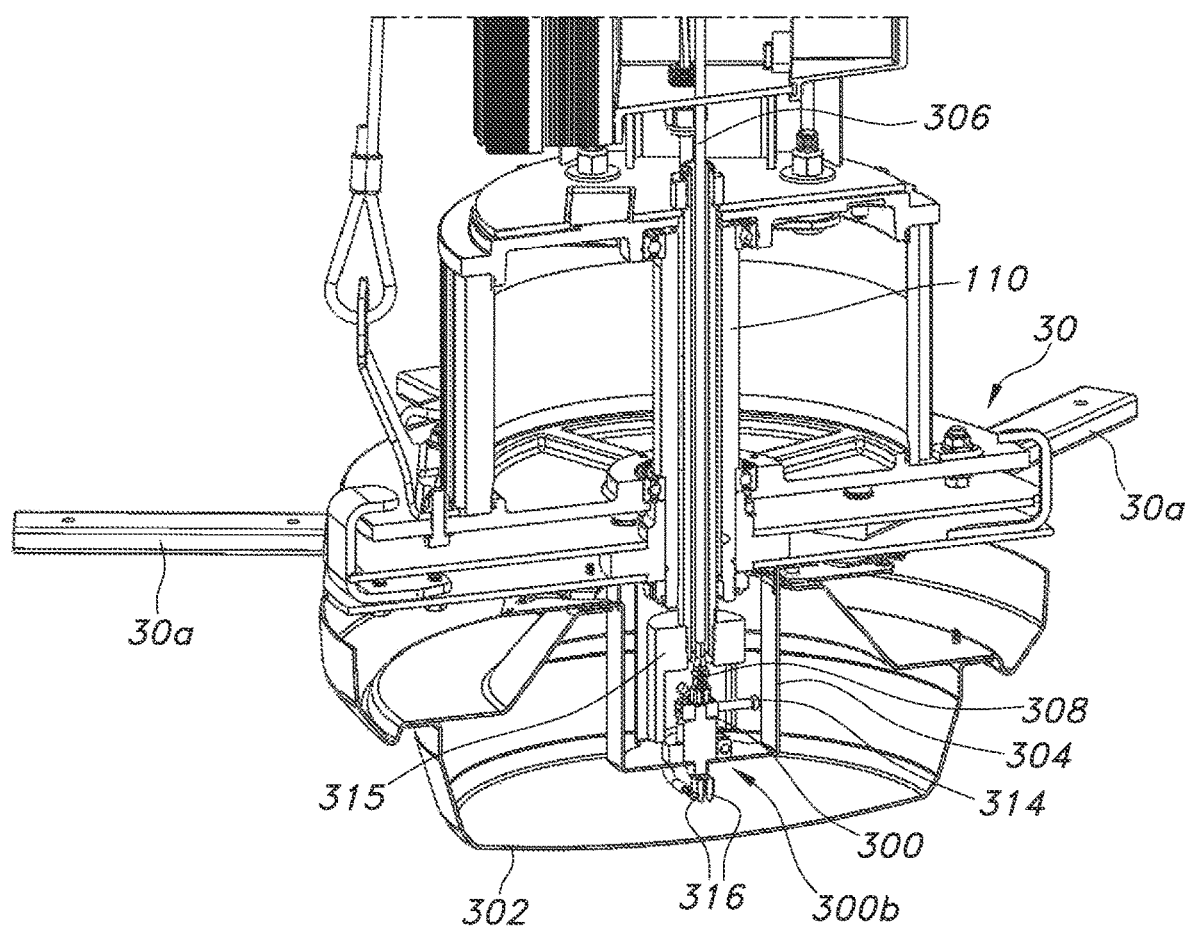
FIGS. 6 and 6A are partially cutaway, partially cross-sectional views of a fan including a rotary coupling for transmitting power to the fan blades.
Figure 6A:
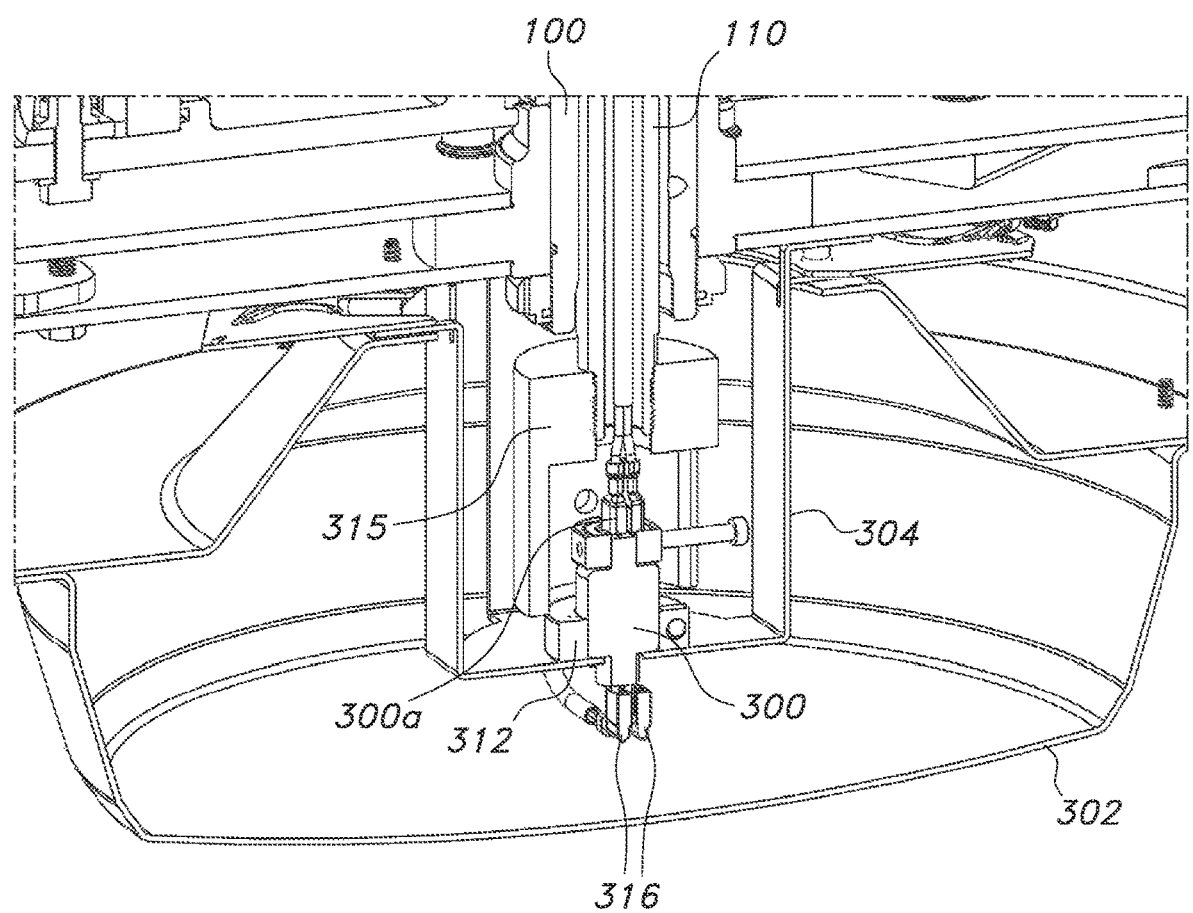
Figure 7:
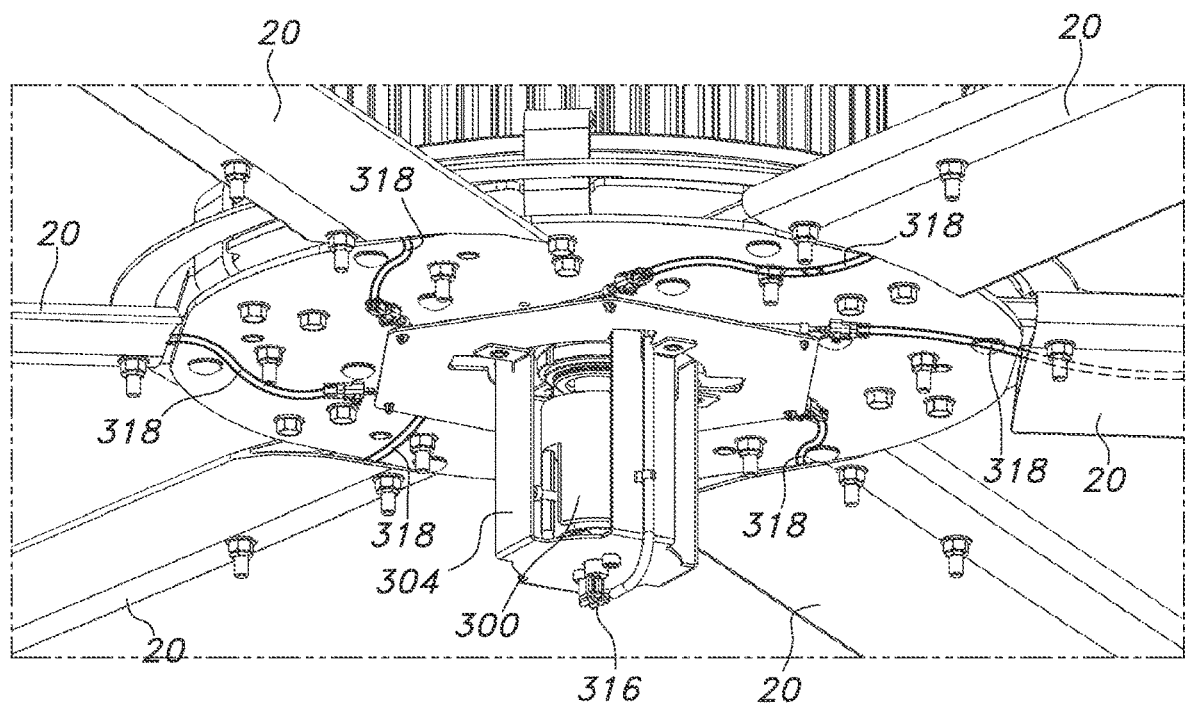
FIG. 7 is a partially cutaway bottom perspective view of a fan including a rotary coupling for transmitting power to the fan blades.
Figure 8:
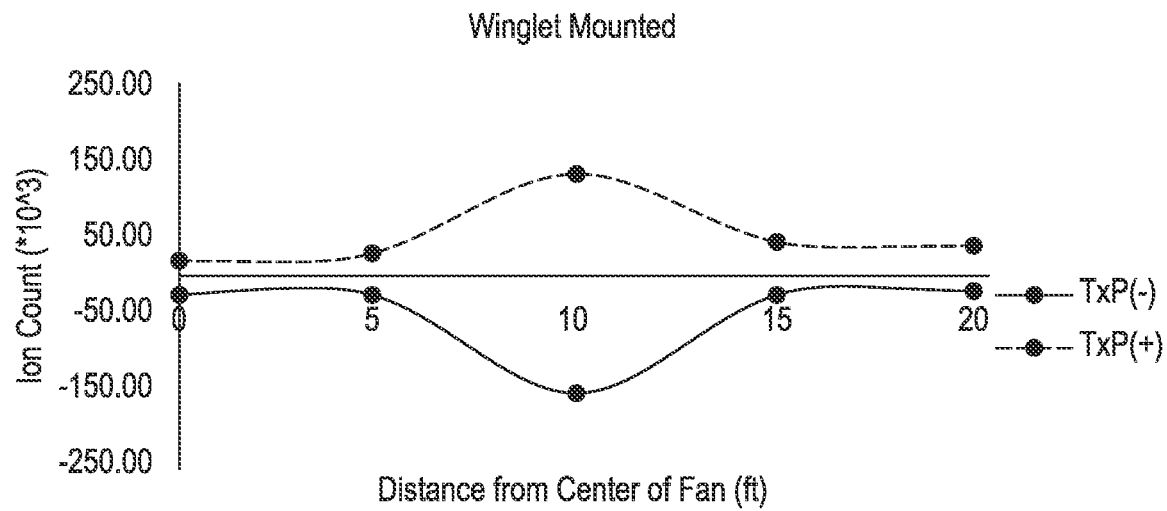
FIGS. 8-11 are graphical illustrations.
Figure 9:
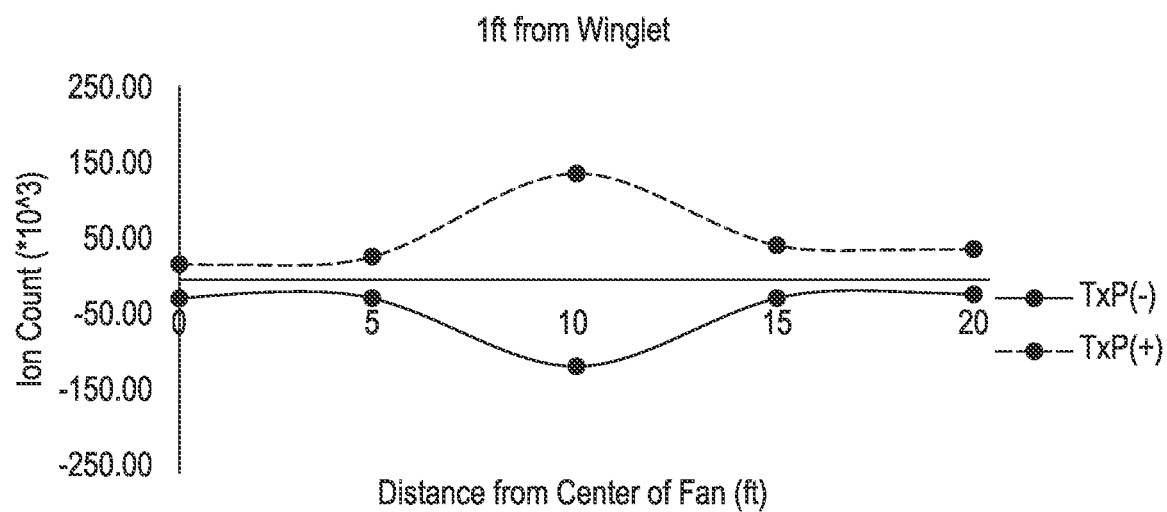
Figure 10:
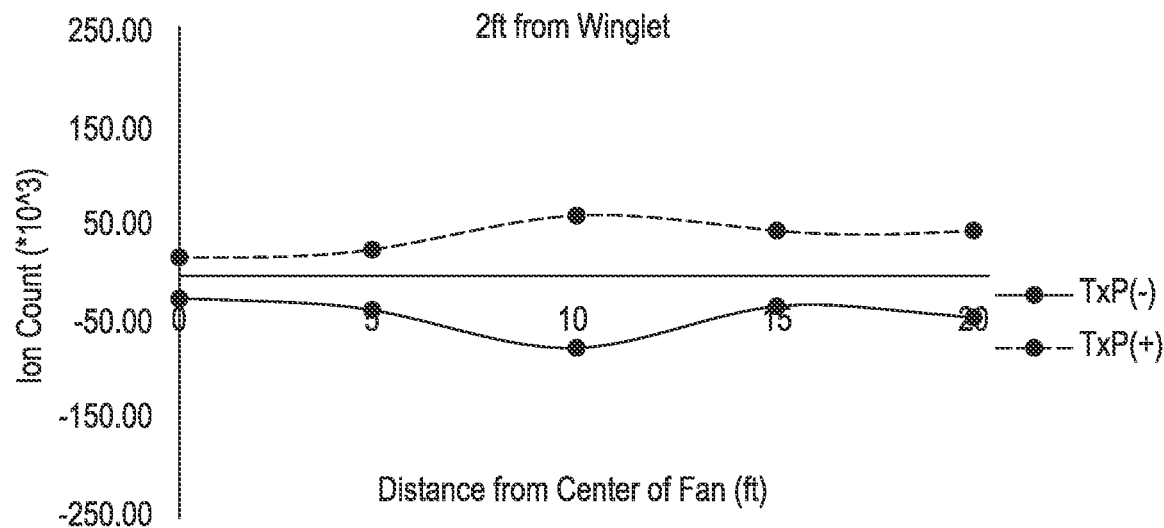
Figure 11:
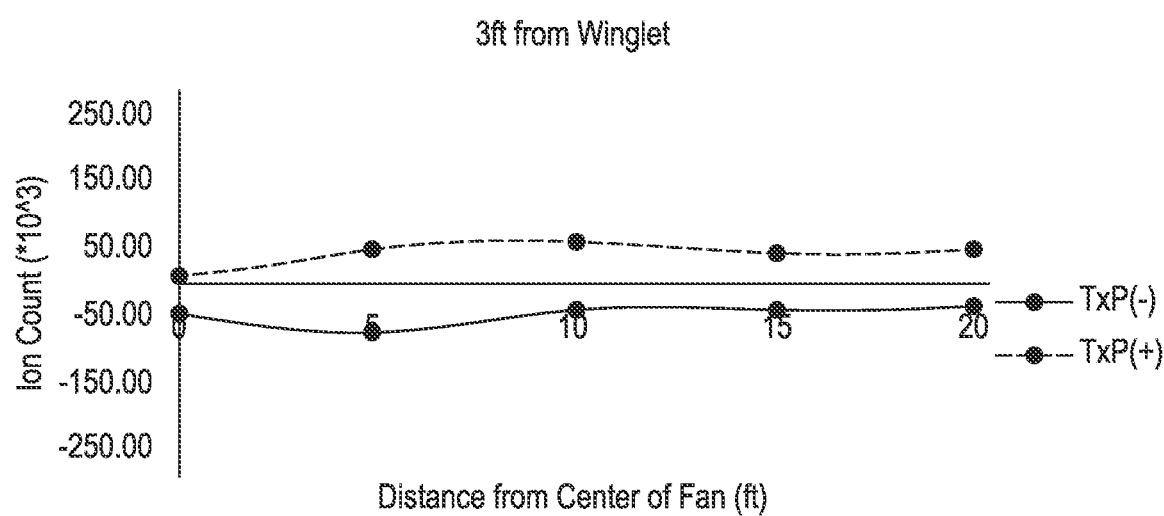

Power for the generator 200 may be supplied via a conduit including a dynamic rotary connector for transmitting power through a rotary coupling, such as a slip ring 3. Turning to FIGS. 6-7, the slip ring 300 may be mounted within a housing 302 supported by the stationary tube 110. such as by a depending support 304. The conduit further comprises a conduit or wires 306 for supplying power from a power source associated with the fan 10 to connectors 308 on the upper portion 300a of the slip ring 300, which is held stationary by a mount 312. A torque arm 314 may be provided for engaging a stop 315 mounted to the tube 110.

The lower portion 300b of the slip ring 300 includes connectors 316. which connect with individual pairs of wires 318 arranged in parallel for conveying power along the fan blade(s) 20 (such as through a channel formed by the hollow interior) to the associated ion generator 200, as can be seen in FIG. 7. Specifically, the wire pairs 318 may extend from a power supply associated with the fan through a channel in the hollow interior of the fan blade 20 to connect to the generator 200. The wire pairs 318 could also extend externally to the fan blade and be fastened (e.g., taped) to the exterior surface thereof.

Figure 5:
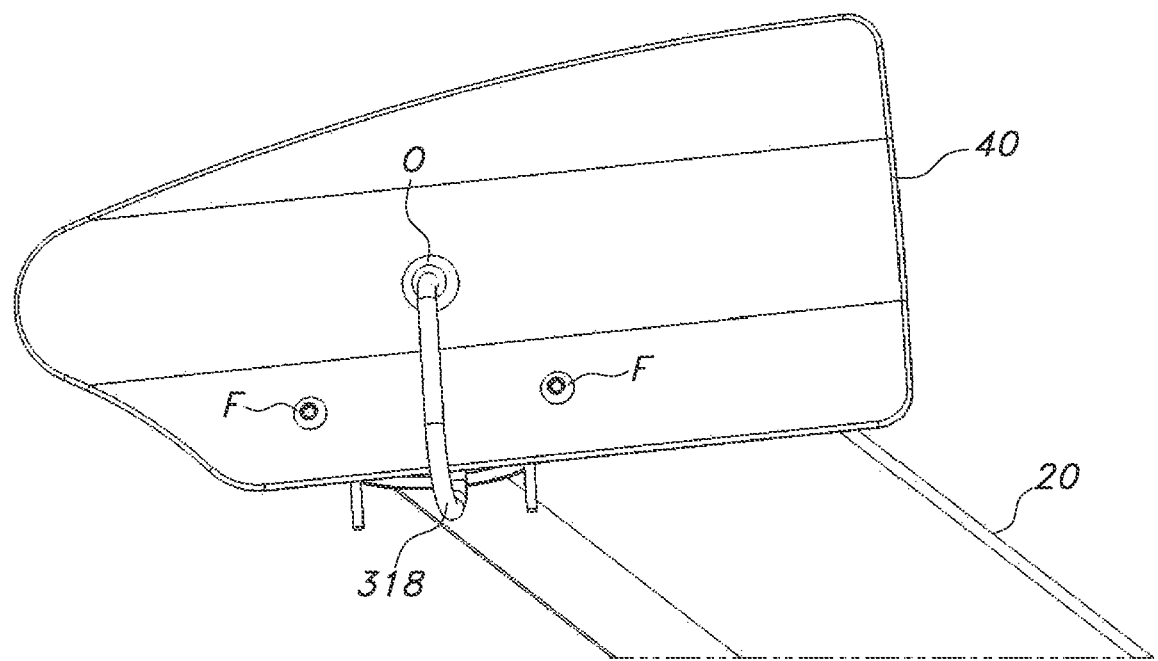
FIG. 5 is a partially cutaway view of an outer face of the winglet.

In the case where the generator 200 is mounted to the winglet 40 as shown, the wires 318 may pass through an opening O in the winglet 40 (see FIG. 5). Thus. when the fan 10 is actuated to cause hub 30 to rotate, the lower portion 300b of the slip ring 300 may also rotate while the upper portion 300a remains stationary. Nevertheless, the power connection and transmission remain continuous and hence dynamic ion generation occurs in a most efficient and effective manner as compared to a stationary source.

FIG. 1 illustrates an example where the generator 200 is carried by the fan blade 20, rather than the winglet 40 itself. In this case, electrical communication may be achieved by wires passing through or along the fan blade 20. In the case of interior passage of wires, the connection with the generator 200 may be made through an opening in the fan blade 20 suitable to allow for the wires to alight therefrom.

Example

In order to test the efficacy of the proposed fan and also confirm optimal positioning of the germicidal generator, a test stand that locate and ion meter and air speed sensor are located 43 inches above the floor. Testing was completed for four different ion generator positions along the length of a fan blade on a fan according to the disclosure, using multiple positions of the test stand from the center of the fan and different ion generator samples. The ion density and air speed were recorded at five locations for each position. The starting position was the center of the fan. Each additional point was a five-foot incremented point in a straight line from the center ending twenty feet from the center of the fan. These points were marked with tape on the floor for consistency, and the test stand was placed just behind the yellow tape marker on the ground for each test. For the purposes of the test, an area under and around the fan was cleared and cleaned so that nothing would interfere with the air flow or ion readings. The HVAC system was also set to off and the automatic fan setting was set to zero. Whenever possible the HVAC and fan were turned back on while the test configuration needed to be adjusted so that the room conditions would remain relatively similar. The test fan was set to 50% power and the resulting RPM was recorded to be 52.4. Prior to commencing testing, the fan was turned on for at least five minutes, which allowed the airflow in the room to settle before testing began.

Data was collected for the test including the positive and negative ion count at five different locations for each position on the winglet. This was recorded alongside the temperature and air flow at each location. At the start of each position a room temperature and relative humidity were recorded.

The test results were recorded with the base position listed as 0 which denotes how far from the distal or winglet end of the fan blade the generator is in feet. Position 1 which is listed in the data tables as 1 in order to represent that it is one foot from the end of the fan blade.

From the following table, it can be appreciated that the highest ion density values were achieved at or closest (0'-1') to the winglet at the end of the fan blade:

| Ion Density/Distance from Winglet | 0' | 1' | 2' | 3' |
|---|---|---|---|---|
| 0 (−) | −25.53 | −25.58 | −25.60 | −51.12 |
| 5 (−) | −28.97 | −23.44 | −38.47 | −77.74 |
| 10 (−) | −161.20 | −118.66 | −75.44 | −47.27 |
| 15 (−) | −30.88 | −24.33 | −32.96 | −44.66 |
| 20 (−) | −26.11 | −27.59 | −43.54 | −41.15 |
| 0 (+) | 18.20 | 20.74 | 20.17 | 5.25 |
| 5 (+) | 27.01 | 29.16 | 25.85 | 47.41 |
| 10 (+) | 132.34 | 146.97 | 61.78 | 56.43 |
| 15 (+) | 43.71 | 45.10 | 47.37 | 42.37 |
| 20 (+) | 37.73 | 40.87 | 46.48 | 47.19 |
| Temp (F.) | 73.73 | 71.92 | 72.48 | 73.22 |
| RH (%) | 45.20 | 45.00 | 45.20 | 45.00 |

The results are illustrated graphically in FIGS. 8-11, and demonstrate the optimal positioning of the ion generator 200 according to one aspect of the disclosure. However, as can be understood, ion generation was still achieved at other blade positions, and is believed to be adequate to provide a desirable level of germicidal capabilities to the fan. It should also be understood that the ion generators may be provided at a different position along each fan blade to vary the amount and field of ion generation.

Summarizing, this disclosure relates to the following items:

1. A fan for improving air quality, comprising:
   (a) a motor;
   (b) a rotatable hub coupled to the motor;
   (c) at least one fan blade comprising: i, a first end coupled to the rotatable hub. ii, a second end radially distant from the rotatable hub, and iii, a winglet attached to the second end; and
   (d) at least one ion generator carried by the winglet.

2. The fan of item 1, wherein the at least one ion generator is mounted to an inner face of the winglet.

3. The fan of item 1 or item 2, wherein the at least one ion generator is mounted to the winglet below a plane of the at least one fan blade.

4. The fan of any of items 1-3. further including a rotary coupling for transmitting power to the at least one ion generator.

5. The fan of claim 4, further including a stationary tube passing through the hub for conveying power to the at least one ion generator, the rotary coupling connected to the stationary tube.

6. The fan of any of items 1-5, wherein a conduit for supplying power for the ion generator passes from the hub, along the at least one fan blade, and to the winglet to connect to the at least one ion generator.

7. The fan of any of items 1-6. wherein the at least one blade includes a passage extending from the first end to the second end, the passage including wires for transmitting power to the at least one ion generator through the winglet.

8. The fan of any of items 1-7, further including a plurality of fan blades coupled to the rotatable hub, each having a winglet including an ion generator.

9. The fan of any of items 1-8. wherein the at least one fan blade has a length of greater than about six feet.

10. A fan for improving air quality, comprising:
   (a) a motor;
   (b) a rotatable hub coupled to the motor;
   (c) at least one fan blade comprising: i, a first end portion coupled to the rotatable hub, ii, a second end portion radially distant from the rotatable hub;
   (d) at least one ion generator carried by the fan blade, such as only at the second end portion; and
   (e) a rotary coupling for transmitting power to the at least one germicidal generator.

11. The fan of item 10, further including a winglet at the second end of the fan blade for carrying the at least one ion generator.

12. The fan of item 10 or item 11, wherein the at least one ion generator is mounted to an inner face of the winglet.

13. The fan of any of items 10-12, wherein the at least one ion generator is mounted to the winglet below a plane of the at least one fan blade.

14. The fan of any of items 10-13, wherein the fan blade is hollow, and further including a wire passing from the rotary coupling through the hollow fan blade to the at least one ion generator.

15. The fan of item 14, further including a stationary tube passing through the hub for conveying power to the at least one ion generator, the rotary coupling connected to the stationary tube.

16. The fan of any of items 10-15. wherein a conduit for supplying power passes from the hub, along the at least one fan blade, and to the at least one ion generator.

17. The fan of any of items 10-16. wherein the at least one blade includes a passage extending from the first end to the second end, the passage including wires for transmitting power to the at least one ion generator through the winglet.

18. The fan of any of items 10-17, further including a plurality of fan blades coupled to the rotatable hub, each having a winglet including an ion generator.

19. The fan of any of items 10-18, wherein the at least one fan blade has a length of greater than about six feet.

20. A fan for improving air quality. comprising:
   (a) a motor;
   (b) a rotatable hub coupled to the motor;
   (c) at least one fan blade comprising: i, a first end coupled to the rotatable hub, ii, a second end radially distant from the rotatable hub;
   (d) at least one ion generator for generating germicidal energy connected to the at least one fan blade; and
   (e) a stationary tube passing through the rotatable hub including a conduit for transmitting power; and
   (f) a rotary coupling for transmitting power from the conduit to the at least one ion generator.

21. The fan of item 20, further including a winglet at the second end of the fan blade for carrying the at least one germicidal generator.

22. The fan of item 20 or item 21, wherein the at least one ion generator is mounted to an inner face of the winglet.

23. The fan of any of items 20-21, wherein the at least one ion generator is mounted to the winglet below a plane of the at least one fan blade.

24. The fan of any of items 20-23, further including a stationary tube passing through the hub for conveying power to the at least one ion generator, the rotary coupling connected to the stationary tube.

25. The fan of any of items 20-24, wherein a conduit for supplying power for the at least one ion generator passes from the hub, along the at least one fan blade, and to the at least one ion generator.

26. The fan of any of items 20-25, wherein the at least one blade includes a passage extending from the first end to the second end, the passage including wires for transmitting power to the at least one ion generator through a portion of the at least one blade.

27. The fan of any of items 20-26, further including a plurality of fan blades coupled to the rotatable hub, each having a winglet including an ion generator.

28. The fan of any of items 20-27, wherein the at least one fan blade has a length of greater than about six feet.

29. A fan for improving air quality. comprising:
   (a) a motor;
   (b) a rotatable hub coupled to the motor
   (c) at least one hollow fan blade comprising: i, a first end portion coupled to the rotatable hub, ii, a second end portion radially distant from the rotatable hub;
   (d) at least one ion generator carried by and external of the fan blade; and
   (e) a wire extending to the at least one ion generator via the hollow fan blade.

30. The fan according to item 29, wherein the at least one ion generator is located at the second end portion of the fan blade.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

Each of the following terms written in singular grammatical form: "a", "an", and "the", as used herein. means "at least one", or "one or more". Use of the phrase "One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and a plurality of steps or procedures. respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of" and "consists of, as used herein, means "including and limited to". The phrase "consisting essentially of" means that the stated entity or item (system. system unit, system sub-unit device, assembly. sub-assembly, mechanism, structure, component element or, peripheral equipment utility, accessory, or material, method or process, step or procedure. sub-step or sub-procedure). which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

Terms of approximation, such as the terms about, substantially, approximately, generally, etc., as used herein, refer to ±10% of the stated numerical value or as close as possible to a stated condition.

It is to be fully understood that certain aspects, characteristics, and features, of the invention. which are, for clarity, illustratively described and presented in the context or format of a plurality of separate embodiments, may also be illustratively described and presented in any suitable combination or sub-combination in the context or format of a single embodiment. Conversely. various aspects, characteristics, and features, of the invention which are illustratively described and presented in combination or sub-combination in the context or format of a single embodiment may also be illustratively described and presented in the context or format of a plurality of separate embodiments.

The invention claimed is:

1. A fan for improving air quality, comprising:
   (a) a motor;
   (b) a rotatable hub coupled to the motor;
   (c) at least one fan blade comprising: i, a first end coupled to the rotatable hub, ii, a second end radially distant from the rotatable hub, and iii, a winglet attached to the second end; and
   (d) at least one ion generator carried by the winglet.

2. The fan of claim 1, wherein the at least one ion generator is mounted to an inner face of the winglet.

3. The fan of claim 1, wherein the at least one ion generator is mounted to the winglet below a plane of the at least one fan blade.

4. The fan of claim 1, further including a rotary coupling for transmitting power to the at least one ion generator.

5. The fan of claim 4, further including a stationary tube passing through the hub for including a conduit for providing power to the at least one ion generator, the rotary coupling connected to the stationary tube.

6. The fan of claim 1, wherein a conduit for supplying power for the at least one ion generator passes from the hub, along the at least one fan blade, and to the winglet to connect to the at least one ion generator.

7. The fan of claim 1, wherein the at least one fan blade includes a passage extending from the first end to the second end, the passage including wires for transmitting power to the at least one ion generator through the winglet.

8. The fan of claim 1, wherein the at last one fan blade comprises a plurality of fan blades coupled to the rotatable hub, each having a winglet including an ion generator.

9. The fan of claim 1, wherein the at least one fan blade has a length of greater than about six feet.

10. A fan for improving air quality, comprising:
    (a) a motor;
    (b) a rotatable hub coupled to the motor;
    (c) at least one fan blade comprising: i, a first end portion coupled to the rotatable hub, ii, a second end portion radially distant from the rotatable hub, and iii, a winglet adjacent the second end portion;
    (d) at least one ion generator carried by the winglet; and
    (e) a rotary coupling for transmitting power to the at least one ion generator.

11. The fan of claim 10, wherein the winglet is at least partially inserted into the second end portion of the at least one fan blade and attached to the at least one ion generator.

12. The fan of claim 11, wherein the at least one ion generator is mounted to an inner face of the winglet.

13. The fan of claim 11, wherein the at least one ion generator is mounted to the winglet below a plane of the at least one fan blade.

14. The fan of claim 10, wherein the at least one fan blade is hollow, and further including a wire passing from the rotary coupling through the at least one hollow fan blade to the at least one ion generator.

15. The fan of claim 14, further including a stationary tube passing through the hub for providing power to the at least one ion generator via a conduit, the rotary coupling connected to the stationary tube.

16. The fan of claim 10, wherein a conduit for supplying power passes from the hub, along the at least one fan blade, and to the at least one ion generator.

17. The fan of claim 10, wherein the at least one fan blade includes a passage extending from the first end to the second end, the passage including wires for transmitting power to the at least one ion generator through the winglet.

18. The fan of claim 10, wherein the at last one fan blade comprises a plurality of fan blades coupled to the rotatable hub, each having a winglet and an ion generator.

19. The fan of claim 10, wherein the at least one fan blade has a length of greater than about six feet.

20. A fan for improving air quality, comprising:
(a) a motor;
(b) a rotatable hub coupled to the motor;
(c) at least one fan blade comprising: i, a first end coupled to the rotatable hub, ii, a second end radially distant from the rotatable hub, and iii, a winglet adjacent the second end;
(d) at least one ion generator for generating germicidal energy carried by the winglet; and
(e) a stationary tube passing through the rotatable hub including a conduit for transmitting power; and
(f) a rotary coupling for transmitting power from the conduit to the at least one ion generator.

21. The fan of claim 20, wherein the at least one ion generator is mounted to an inner fee portion of the winglet facing the hub.

22. The fan of claim 20, wherein the at least one ion generator is mounted to the winglet below a plane of the at least one fan blade.

23. The fan of claim 22, wherein the conduit passes through the stationary tube for providing power to the at least one ion generator, the rotary coupling connected to the stationary tube.

24. The fan of claim 20, wherein the conduit for supplying power for the at least one ion generator passes from the hub, along the at least one fan blade, and to the at least one ion generator.

25. The fan of claim 20, wherein the at least one fan blade includes a passage extending from the first end to the second end, the passage including wires for transmitting power to the at least one ion generator through a portion of the at least one fan blade.

26. The fan of claim 20, wherein the at last one fan blade comprises a plurality of fan blades coupled to the rotatable hub, each having a winglet including an ion generator.

27. The fan of claim 20, wherein the at least one fan blade has a length of greater than about six feet.

28. A fan for improving air quality, comprising:
(a) a motor;
(b) a rotatable hub coupled to the motor;
(c) at least one hollow fan blade comprising: i, a first end portion coupled to the rotatable hub, ii, a second end portion radially distant from the rotatable hub, and iii, a winglet;
(d) at least one ion generator carried external to the at least one hollow fan blade and carried by the winglet; and
(e) a wire extending to the at least one ion generator via the at least one hollow fan blade.

29. The fan according to claim 28, wherein the at least one ion generator is located at the second end portion of the at least one hollow fan blade.

30. The fan according to claim 28, wherein the wire extends at least partially through a longitudinally extending passage within the at least one hollow fan blade.

* * * * *

UNITED STATES PATENT AND TRADEMARK OFFICE
CERTIFICATE OF CORRECTION

PATENT NO. : 11,027,038 B1
APPLICATION NO. : 17/147086
DATED : June 8, 2021
INVENTOR(S) : Lennie Rhoades et al.

It is certified that error appears in the above-identified patent and that said Letters Patent is hereby corrected as shown below:

In the Claims

Claim 1, Column 12, Line 29, please replace "i," with --i.--
Claim 1, Column 12, Line 30, please replace "ii," with --ii.--
Claim 1, Column 12, Line 31, please replace "iii," with --iii.--

Claim 10, Column 12, Line 61, please replace "i," with --i.--
Claim 10, Column 12, Line 62, please replace "ii," with --ii.--
Claim 10, Column 12, Line 63, please replace "iii," with --iii.--

Claim 20, Column 13, Line 33, please replace "iii," with --iii.--
Claim 20, Column 13, Line 34, please replace "ii," with --ii.--
Claim 20, Column 13, Line 35, please replace "iii," with --iii.--

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*